United States Patent [19]

Liu

[11] Patent Number: 4,842,859

[45] Date of Patent: Jun. 27, 1989

[54] PHARMACEUTICAL COMPOSITIONS FOR REDUCING HYPERLIPIDEMIA AND PLATELET-AGGREGATION

[76] Inventor: Yaguang Liu, 67-08, 168th St., Flushing, N.Y. 11365

[21] Appl. No.: 905,554

[22] Filed: Sep. 8, 1986

[51] Int. Cl.$^4$ .............................................. A61K 3/78
[52] U.S. Cl. ............................... 424/195.1; 424/107; 514/456; 514/558; 514/570; 514/679; 514/822
[58] Field of Search ................ 424/195.1, 95, 107; 514/456, 679, 570, 558, 822

[56] References Cited

FOREIGN PATENT DOCUMENTS 0049097 3/1985 Japan ................................. 514/558

OTHER PUBLICATIONS

Chem Abst. 94:266g, 1981.
Chem Abst. 102:23456s, 1985.
Chem Abst. 103:64594z, 1985.
Chem Abst. 154:28637c, 1986.

*Primary Examiner*—John W. Rollins
*Attorney, Agent, or Firm*—Chen Patents

[57] ABSTRACT

The new pharmaceutical compositions and processes are provided for reducing both hyperlipidemia and platelet-aggregation (PHP).

The fine-PHP is composed of following ingredients: Scoparone or Aurapten, Curcumin, Ferulic Acid, Yejuhua-flavonoid and additive ingredient—fish oil. The compositions are nontoxic.

6 Claims, No Drawings

PHARMACEUTICAL COMPOSITIONS FOR REDUCING HYPERLIPIDEMIA AND PLATELET-AGGREGATION

BACKGROUND OF THE INVENTION

The present invention relates to pharmaceutical compositions useful for reducing hyperlipidemia and platelet-aggregation. The bifunctional pharmaceutical compositions are nontoxic.

Specifically, this invention provides new compositions of five major active ingredients.

1. Aurapten or scoparone is extracted from peels, seeds or young plants of citrus aurantium L., citrus spp., Poncirus trifoliata raf or Artemisia Capillaris Thunb.
2. Curcumin is extracted from Curcuma longa L., Curcuma aromatica salisb or Curcuma zedoaria roscoe.
3. Ferulic acid is extracted from Levisticum officinale koch, Angelica sinensis Diels or Angelica spp.
4. Yejuhua-flavonoid is extracted from Matricaria chamomilla L, Tagetes minuta L, Tagetes patula L or Chrysanthemum indicum L.

The herbs: Citrus aurantium L, Citrus spp, Curcuma longa L, Levisticum officinale koch, Angelica spp, Matricaria chamomilla L, Tagetes minuta L and Tagetes patula L are recognized by The U.S. Food and Drug Administration (FDA) as safe for human consumption.

5. Additive ingredient: fish oil concentrate derived from the fish body (including scales of a fish).

DESCRIPTION OF THE PRIOR ART

Some drugs have been used for decreasing levels of cholesterol and triglyceride: for example, Clofibrate, Gemfibrozil, Questran, Colestipol and Neomycin in particular, for decreasing cholesterol and triglyceride levels in hypercholesterol and hypertriglyceridemia.

However, all the above as mentioned drugs have a certain degree of side effects. Clofibrate and Gemfibrozil have the following side effects: nausea, abdominal discomfort, gastrointestinal discomfort, myalgia associated with increased plasma levels of creatine phosphokinase. In addition, hepatic dysfunction and bone marrow depression are toxic effects of the drugs. Patients taking clofibrate are reported to have decreased libido and breast tenderness. Brittle hair and alopecia have also been reported. Questran and, colestipol have the following side effects: the most common complaints are constipation and bloating sensation; some times hearburn and diarrhea also are reported. Neomycin has high toxicity. Even at low doses, nausea, abdominal cramps, diarrhea and malabsorption have been reported.

As mentioned above, so far there is no effective and safe drug which would decrease high cholesterol and triglyceride levels in the plasma of patients and without side effects.

Few drugs have been shown to decrease platelet aggregation. For example, Aspirin has been shown to decrease the incidence of transient ischemic attacks in men and has been used as prophylatic agent for this purpose. Aspirin has the same drawbacks as the above drugs for decreasing cholesterol and triglyceride, Aspirin taken at the usual dosage, causes the main side effect of gastric intolerance. With higher doses, patients may experience tinnitus, decreased hearing and vertigo. The adverse effects of aspirin on renal function and on liver has been reported. Hypersensitivity reactions may occur in patients with asthma and nasal polyps and may be associated with bronchoconstriction and shock. Aspirin has serious side effects on patients with hemophilia.

In tradition, Curcuma longa L. Angelica sinesis diels and Artemisia capillaris thunb as natural herbs have been used in clinic for decreasing levels of hyperlipidemia and anti-aggregating activity of platelet.

Reference:

| | | |
|---|---|---|
| (1) Chung King Medical College Acta | 1:88 | 1979 |
| (2) New Medical Journal | 11:35 | 1977 |
| (3) Journal of Traditional Chinese Medicine | 21:39 | 1980 |
| (4) Journal of Traditional Chinese Medicine | 23:762 | 1982 |

SUMMARY OF THE INVENTION

It is an object of the present invention to provide pharmaceutical compounds and compositions which are safe and highly effective for reducing hyperlipidemia and inhibiting platelet aggregation.

These objects and other objects will become apparent hereinafter, upon reading the detailed description of the invention. The present invention resides, briefly stated, in new compositions comprising a mixture of the following active ingredients:

(1) Aurapten or Scopatone extracted from peels, seeds or young plants of Citrus aurantium L, Citrus spp, Poncirus trifoliata raf or Artemisia capillaris Thunb.

(2) Curcumin extracted from Curcuma longa L, Curcuma aromatica salisb or Curcuma zedoaria roscoe.

(3) The Ferulic Acid extracted from Levisticum officinale koch, Angelica sinensis Diels, or Angelica spp.

(4) Yejuhua-flavonoid extracted from Matricaria chamomilla L, Tagetes minuta L, Tagetes Patula L or Chrysanthemum indicum L.

(5) Additive ingredient: Fish oil concentrate.

For the sake of convenience, compositions comprising mixtures of the above extracts will hereinafter be referred to as "PHP".

The following herbs: Levisticum officinale koch, Matricaria chamomilla L, Citrus aurantium L, Citrus spp, Curcuma longa L, Angelica spp, Tagetes minuta L and Tagetes patula L are recognized by FDA of U.S. as safe for human consumption.

DETAILED DESCRIPTION

Among all the diseases today in the entire world, coronary artery disease and cerebrovascular accident bring about the highest mortality. Coronary artery disease and cerebrovascular accident are believed to involve following mechanisms: hyperlipidemia and high platelet-aggregation.

Obviously, reducing hyperlipidemia and inhibiting platelet aggregation are both very important. Consequently the aim of the present invention is to provide for new and safe therapeutic compounds which will fulfill practical needs more effective than previously known drugs in that the compounds not only reduce hyperlipidemia both also inhibit platelet aggregation at the same time.

Therefore PHP is a bifunctional drug. So far some drugs used for reducing hyperlipidemia and other drugs used for inhibiting platelet aggregation only. Meanwhile all the mentioned drugs have a certain degree side effect.

Coronary artery diseases and cerebrovascular accident are caused by hyperlipidemia and high platelet-aggregation. Therefore PHP can effectively treat and prevent coronary artery disease and cerebrovascular accident.

PHP can be administered to patients in the form of capsules containing a powdered mixture of the active ingredients in appropriate proportions. Alternatively, tablets can be prepared comprising the active ingredients and pharmaceutically acceptable binders, excipients, lubricants, sweeteners and coatings. A syrup or elixir may be prepared by dissolving PHP in alcohol and water together with suitable preservatives, sweeteners, dyes and flavoring agents. Ampules or vials for injection may likewise be prepared, with the PHP prepared as for oral administration and after being purified through further recrystallization and sterilization and with the addition thereto of distilled water and other suitable solvents and additives known in the pharmaceutical art.

The PHP dosage units prepared according to the invention can be administered to patients. PHP is non-toxic.

The compositions of the present invention all include as their active component PHP, which as indicated previously, consists of a mixture of four plant extracts: Aurapten or Scoparone, Curcumin, Yejuhna-flavonoid, Ferulic acid and additive ingredient: fish oil concentrate. Aurapten and Scoparone have following structural formula:

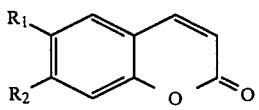

When $R_1=CH_3O$, $R_2=CH_3O$, the compound is scoparone. When $R_1=H$

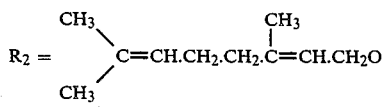

the compound is aurapten.

Curcumin has following structural formula:

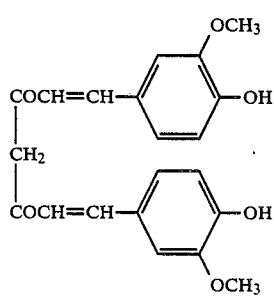

Ferulic acid has the following structural formula:

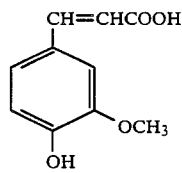

The fish oil concentrate is derived from the fish body (include scales of fish). Fish oil is rich in Eicosapentaenoic acid (EPA) and Docosahexaenoic acid (DHA).

EPA is the precursors in the synthesis of prostaglandins which may help antiplatelet-aggregating activity and help prevent thrombosis.

The following specific examples will provide detailed illustrations of methods of producing PHP according to the present invention and pharmaceutical dosage units containing PHP. Moreover, examples will be given for pharmaceutical testing performed with PHP which demonstrates its effectiveness in reducing hyperlipidemia and reducing platelet-aggregation. These examples are not intended, however, to limit or restrict the scope of the invention in any way, and should not be construed as providing conditions, parameters, reagents, or starting materials which must be utilized exclusively in order to practice the present invention.

EXAMPLE 1

Scoparone extracted from young plants of Artemisia capillaris Thunb

Young plants of Artemisia Capillaris Thunb were dried and powdered. One kilogram (kg) of the powder was dipped in 3 liters of 95% ethanol for about 12 hours at 50° C. The resultant ethanol extract was concentrated under reduced pressure by distillation. A residue was recovered and dissolved in 300 ml 50° C.-water. The resulting aqueous solution was washed twice with chloroform. The solution was heated to remove the chloroform. Then, the solution was extracted twice with aceticether. Aceticether extract was removed and dried by sodium sulfate. Aceticether was then recovered by reduced pressure distillation and the residue was dissolved in warm-methanol. The methanol solution was concentrated, and was allowed to stand at room temperature overnight. White or white-yellow crystals were formed. The crystals were recrystallized from methanol and water. They were dried under vacuum and found to have a melting point of 145°–146° C. The resulting white or white-yellow crystals was the final product: scoparone.

EXAMPLE 2

Extraction of Curcumin

Rhizome of Curcuma Longa L., Curcuma aromatica Salisb or Curcuma Zedoaria Rosco was dried and powdered. One kilogram of the powder was soaked in 5 liters of 95% ethanol, for about 12 hours at room temperature. The resulting ethanol extract was filtered. Ethanol was then recovered under reduced pressure distillation. A residue was dissolved in 300 ml of 1N NaOH, then the resulting solution was adjusted to pH 7 with 1N HCl, and a light yellow precipitate was formed. The precipitate was dissolved in 300 ml of 95% ethanol and the last procedure was repeated to form a light yellow precipitate again. The light yellow precipitate was washed with water, acetone and ether successively. The final light yellow powder was dried under vacuum and was found to have a melting point of 183° C.

EXAMPLE 3

Ferulic acid extracted from Levisticum Officinale Koch or Angelica sinensis diels 1 kg of dried powder of Levisticum Officinale Koch or Angelica sinensis Diels is extracted with 5000 ml of boiling water for 1 hour. The extraction is repeated twice. Extracts are combined and distilled to 1000 ml by reduced pressure distillation. Add 2000 ml 95% ethanol to 1000 ml the residue with stir. Set 24 hours. Ethanol mixture is filtered and the filtrate is concentrated to syrup under reduced pressure distillation. Add 300 g silica gel to the syrup which mixture is cooled to the room temperature and dried at 60° C. Dried powders are washed with 95% ethanol in a percolator until ethanol becomes light color. Ethanol washes are combined and distilled under reduced pressure. Whereby ethanol is recovered and a still residue is obtained. This still residue is dissolved in 200 ml of distilled water. This aqueous solution is added to a column packed with polyamide resin. The column is washed with distilled water, and followed by 50% ethanol. The 50% ethanol is collected and distilled under reduced pressure. The residue is dissolved in 100 ml of methanol. This methanol solution is added to 5 g silica gel. Dried. The methanol solution is passed through a column (4×22 cm). Wash column by benzolacetone (7:3). The benzol—acetone is combined and distilled under reduced pressure. Crystals are obtained. Crystals are recrystallized again from chloform—methanol (1:1). White crystals are obtained.

Melting point is 169.5°–171° C.

EXAMPLE 4

Extraction of Yejuhua-flavonoid from chrysanthemum indicum L

PLants or flowers of chrysanthemum indicum L were dried and powdered. 1 kg of the powder was extracted in 2 liters of 95% ethanol for about 24 hours at room temperature. The solution was filtered and the extract filtrate saved. 2 liters of 95% ethanol was added to residue and refluxed in water bath and refluxing for 6 hours. The refluxed ethanol was cooled and filtered and the filtrate combined with the extract filtrate. Ethanol was then recovered by reduced pressure distillation and a residue was saved. 1000 ml of aceticether was added to the residue and refluxed in a water bath for 6 hours. The refluxing procedure was repeated. Aceticether was then concentrated under reduced pressure distillation. Crystals were formed. The crystals were washed with water. Final crystals were dried under vacuum and was found to have a melting point of about 250° C.

EXAMPLE 5

Preparation of PHP (1) Fine product of PHP:

Fine PHP prepared according to the present invention consists of about 10%–40% (weight percent) scoparone or aurapten, 10%–40% Ferulic acid, 5%–30% curcumin, 5%–30% yejuhua-flavonoid and 10%–50% fish oil. Preferred composition weight percent according to the present invention consists fo about 25% scoparone or aurapten, 25% ferulic acid, 10% curcumin, 10% yejuhua-flavonoid and 30% fish oil.

The dry ingredients of PHP, prepared in accordance with the present invention, may be incorporated into tablets, capsules, syrups or other form by conventional methods.

(2) Crude product of PHP:

Crude PHP is extracted from the above mentioned plants by ethanol.

Proportion of plants, extracts and an additive for example, as follows (by weight):

| | |
|---|---|
| *Levisticum officinale* Koch or Angelica spp: | 21%, |
| *Artemisia capillaris* Thunb or Citrus spp: | 21%, |
| *Curcuma longa* L or C Aromatica Salissb: | 14%, |
| *Chrysanthemum indicum* L or *Matricaria chamomilla* L: | 14%, |
| Fish oil: | 30%. |

Tissues of plant were dried and powdered. 5 liter of distallatory water was added 1 kg of dried powder. The mixture was heated to boil and simmered for one hour. This water extraction was repeated two times. Aqueous extracts were combined and filtered. The filtrate was concentrated under reduced pressure to approximately 500 ml. Then 1000 ml 95% ethanol was added to the 500 ml aqueous extracts with stirring, which was then distilled and filtered. A residue and a filtrate (A) was obtained. 1000 ml 90% ethanol was added to the residue. With stirring 90% ethanol extraction was repeated twice. The 90% ethanol extracts were combined. Filtered. Filtrate (B) was obtained. Combined filtrate (A) and (B) was concentrated to a syrup by reduced pressure distillation; while ethanol was recovered. The syrup was dried under vacuum and granulated to final powder. The final powder may be combined with fish oil. Weight of every capsule and table is about 100–200 mg. Crude-PHP is similar to fine-PHP in pharmacological property.

EXAMPLE 6

The influence of PHP on aggregation of platelets (1) Methods for blood of animal:

Aggregation of platelet testing: Rabbit blood was sampled by cardiac puncture from rabbit with silicon-coated syringe. The bood was mixed with 3.8% sodium citrate at 9:1 and spun at 1,000 rpm for 6 minutes. 1 ml of the platelet-rich plasma was transfered to a silicon-coated 2 ml cell. Mix well and read for transmittance (Ti), with a spectrophotometer. Then 0.02 ml of ADP (10 $\mu$M) was added. Stir constantly and read for transmittance of the platelet—containing-plasma once by every one minute and obtain the maximal transmittance (Tm) within 10 minutes. Spin the blood sample at 3000 rpm for 45 minutes and read for transmittance. To, of the platelet—poor plasma, the platelet aggregation rate is calculated as follows:

$$\text{Aggregation Rate of Platelet} = \frac{Tm - Ti}{To - Ti} \times 100\%$$

Results were illustrated by following Table 1

| Aggregation rate of platelet (%) | |
|---|---|
| control group (normal saline) | PHP group (1 mg/ml PHP) |
| 50.4 ± 8.1 (*14) | 20.9 ± 1.20 (*14) |

| Aggregation rate of platelet (%) | |
|---|---|
| control group (normal saline) | PHP group (1 mg/ml PHP) |
| P < 0.001 | |

Table 1 as shown above: the influence of PHP on aggregation of platelets in vivo. * indicates number of sample.

(2) Methods for blood of humans:

Blood was collected from veins of humans using a needle attached to a plastic disposal syringe. the blood was immediately transferred into siliconized glass tube containing 0.1 volume of 3.13% sodium citrate. Platelet-rich plasma (PRP) was obtained by centrifugation of the whole blood at 1000 rpm for 10 min at room temperature. Platelet-poor plasma (PPP) was prepared by centrifugation of the remaining blood at 3000 rpm for 10 min. Platelet aggregation was performed using in aggregameter at 37° C. Human platelet studies were carried out at constant platelet number ($3 \times 10^8$/ml). With regards to determination of platelet aggregation, the maximum aggregation induced by adenosine diphosphate (ADP) in a final concentration of 2 $\mu$M was obtained by the light transmission method. 0.4 ml PRP of elach subject was introduced into each of 24 tubes and divided into 2 groups. Then to the 12 tubes of each group were added 50 $\mu$l of saline and 50 $\mu$l PHP (0.5 mg/ml) respectively. After incubation of 3 min at 37° C., to each of 12 tubes of each group were added 50 $\mu$l of 2 $\mu$M ADP. A 5 minutes aggregation curve for each tube was plotted.

Percent inhibition of aggregation by PHP was calculated by:

$$\% \text{ inhibition of aggregation} = \frac{\% \text{ aggregation in control} - \% \text{ aggregation with PHP}}{\% \text{ aggregatio in control}} \times 100$$

Statistical analysis of the results was carried out using Student's t-test for paired data.

Table 2 Effect of PHP on inhibition of aggregation of platelet

| | Rate of aggregation of platelet | Percent inhibition of aggregation |
|---|---|---|
| Control | 67.5 ± 5.0 | — |
| PHP | 20.9 ± 0.9 | 69.0% |
| P | <0.01 | |

EXAMPLE 7

The influence of PHP on lowering heperlipidemia

As test animals 30 male mice weighing of 12-22 grams (g) were used. They were divided into the following three groups. Each group consists ten mice.

(A) Standard group

Each animal in standard group is given a daily 0.5 ml of distillatory water by stomach-tube.

(B) Control group

Each animal in control group is given a daily 0.5 ml of cholesterol-emulsion. Cholesterol-emulsion has the follwing materials:

| a. cholesterol | 5 g |
|---|---|
| b. sodium deoxycholate | 0.5 g |
| c. lard | 10 g |
| d. tween | 10 ml |
| e. propylene glycol | 10 ml |
| Water was added | 50 ml. |

(C) PHP group

Each animal in PHP group is given a daily 0.5 ml of cholesterol-emulsion and about 80 mg/kg of PHP. Mice of three groups were nurtured using a standard diet.

The mice of the above three groups were raised for 10 days. At the end of 10-day test period the animals are weighed and sacrificed, serum cholesterol and triglycerides of liver are determined from blood samples thaken from the venae cava. The methods are described as following:

Chemical colorimetric methods have been used in the analysis of serum cholesterol.

(D) Reagents and materials
1. Isopropanol, reagent grade.
2. Adsorbent Mixture for the removal of bilirubin, phospholipids, monoglycerides, diglycerides, glucose, and other chromogenic material. Mix well the following materials:
    a. Alumina 50-100 mesh, 900 g.
    b. Zeolite (Taylor), group and sifted to 20-80 mesh, activated by heating at 110° C. overnight, 50 g.
    c. Lloyd's reagent, 50 g.
    d. $CuSO_4$ anhydrous powder, 10 g.
    e. $Ca(OH)_2$ anhydrous, 20 g.
3. Sulfuric Acid, concentrated, reagent grade.
4. Ferric Chloride Color Reagent. Place 500 mg $FeCl_36H_2O$ in 500 ml volumetric flask, add glacial acetic acid to the mark, and mix. The reagent is stable in the dark for 1 year at room temperature.
5. Cholesterol Standard, 200 mg/dl. Dissolve 200.0 mg cholesterol in isopropanol and make up to 100 ml volume.
6. 20×150 mm screw-capped culture tubes with teflon-lined caps.

(E) Procedure

The development and measurement of the color after preparation of the extract has been made by the following methods:
1. Extraction: Pipet 9.5 ml isopropanol into all culture tubes to be used for samples and controls and 9.0 ml isopropanol plus 0.5 ml water to tubes for standards.
2. Pipet 0.5 ml of serum into the appropriate sample and control tubes and 0.50 ml of cholesterol standard into the standard tubes. Tightly stopper and shake vigorously or mix on a vortex-type mixer for 20 seconds.
3. Allow to stand about 20 minutes, add about 2 g of adsorbent mixture to each tube, and mix thoroughly for 20 seconds. Let stand for 30 minutes, and shake vigorously for 5 second every 10 minutes.
4. Centrifuge for 10 minutes at 1100 to 1200 g. Aliquots of the extract can be used for the determination of cholesterol. Samples with grossly elevated concentrations can be diluted with isopropanol and re-assayed.
5. Color reaction. Prepare a blank by pipetting 1.0 ml of isopropanol into a tube. Transfer 1.0 ml of sample, control, and standard extracts, respectively, into appropriately marked tubes.
6. To each tube, add 2 ml FeCl₃ reagent and mix.
7. Add 2 ml concentrated H₂SO₄ to a tube by allowing the acid to run down the side of the slanted tube, tightly stopper, and mix by inversion 6 times. Then proceed to the next tube.
8. Let color develop for 10 minutes, transfer to a cuvet, and read the absorbance against the blank at 540 nm.
9. Calculations. Let $A_u$ be absorbance of sample and $A_s$ the absorbance of standard; read against the blank.

$$\text{Cholesterol, mg/dl} = \frac{A_u}{A_s} \times 200 \text{ mg/dl}$$

Table 3 Influence of PHP on lowering heperlipidemia

|  | Cholosterol of serum (mg/dl) | Triglyceride of liver (mg/100 g) |
| --- | --- | --- |
| Standard group | 201 ± 15 (10) | 12.2 ± 1.8 (10) |
| Control group | 420 ± 20 (10) | 27.9 ± 4.5 (10) |
| PHP group | 288 ± 18 (10) | 12.4 ± 1.9 (10) |
| P | <0.01 | <0.001 |

EXAMPLE 8

Safety of PHP

10% solution of PHP was administered intraperitoneally in mice. No reactios were observed. The acute $LD_{50}$ was found to be 1050 mg/kg. Each dose for an adult is 20 mg. Using 50 kg as the average weight of an adult the dosage is 0.4 mg/kg, therefore it is very safe.

It will thus be shown that there are provided compositions and methods which achieve the various objects of the invention, and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the appended claims:

1. A crude pharmaceutical composition comprising plant extracts, in weight %, derived from the following plants:
    Artemisia capillaris Thunb, Citrus anrantium L, Citrus spp or Poncirus trifoliata Raf, 20–50
    Angelica spp, Angelica sinensis Diels or Levisticum officinale Kock, 20–50
    Curcuma aromatica salisb, or Curcuma zedoaria roscoe, 5–30 and
    Chrysanthemum indicum L., Matricaria chamomilla L., Tagetes patula L. or Tagetes minmuta L., 5–30.
2. The composition of claim 1 further comprising 10–50 wt % of fish oil.
3. A pharmaceutical composition for reducing hyperlipidemia and inhibiting platelet-aggregation comprising:

| a, Scoparone or Aurapten | 10–40 wt. % |
| --- | --- |
| b, Curcumin | 5–30 wt. % |
| c, Ferulic acid | 10–40 wt. % and |
| d, Yejuhua-flavonoid | 5–30 wt. % |

4. The composition of claim 3 further comprising 10–50 wt. % of fish oil.
5. The composition of claim 3, wherein said scoparone or aurapten is extracted from the peels, seeds of a plant selected from the group consisting of artemisia capillaris Thunb, Citrus spp, Poncirus trifoliata Raf, and Citrus aurantium L.; said curcumin is extracted from a plant selected from the group consisting of Curcuma longa L, Curcuma aromatica salisb, and Curcuma zedoaria roscoe; said ferulic acid is extracted from a plant selected from the group consisting of Levisticum officinale Koch, Angelica sinensis Dielsor and Angelica spp; and said Yejuhua-flavonoid is extracted from a plant selected from the group consisting of Chrysanthemum indicum L., Tagetes patula L., Tagetes minute L. and Matricaria chamomilla.
6. A method for reducing hyperlipidemia and inhibiting platelet-aggregation in a human in need thereof comprising administering to said human an effective dosage of the composition of claim 3.

* * * * *